US009604045B2

(12) United States Patent
Tsoukalis

(10) Patent No.: US 9,604,045 B2
(45) Date of Patent: Mar. 28, 2017

(54) LOCK CONNECTION DEVICE FOR MEDICAL FLUID LINES

(71) Applicant: MICREL Medical Devices S.A., Gerakas (GR)

(72) Inventor: Achilleas Tsoukalis, Gerakas (GR)

(73) Assignee: MICREL MEDICAL DEVICES, S.A., Gerakas (GR)

( * ) Notice: Subject to any disclaimer, the term of this patent is extended or adjusted under 35 U.S.C. 154(b) by 200 days.

(21) Appl. No.: 14/161,128

(22) Filed: Jan. 22, 2014

(65) Prior Publication Data

US 2014/0207118 A1    Jul. 24, 2014

(30) Foreign Application Priority Data

Jan. 22, 2013    (GR) .............................. 20130100031

(51) Int. Cl.
*A61M 39/10*    (2006.01)
*A61M 39/14*    (2006.01)
(Continued)

(52) U.S. Cl.
CPC ........ *A61M 39/1011* (2013.01); *A61M 39/14* (2013.01); *A61M 39/18* (2013.01); *A61M 39/20* (2013.01); *A61M 2039/1027* (2013.01)

(58) Field of Classification Search
CPC .. A61M 39/1011; A61M 39/14; A61M 39/20; A61M 2039/1027;
(Continued)

(56) References Cited

U.S. PATENT DOCUMENTS

| 3,986,508 A * | 10/1976 | Barrington ................ A61L 2/00 |
| | | 222/83 |
| 2003/0144647 A1* | 7/2003 | Miyahara ............ A61M 39/162 |
| | | 604/523 |

(Continued)

FOREIGN PATENT DOCUMENTS

WO    WO03/041789    5/2003

OTHER PUBLICATIONS

Oct. 11, 2016, Office Action dated Oct. 11, 2016 from EP Application No. 14151955.3, 6 pages.

*Primary Examiner* — Laura Bouchelle
*Assistant Examiner* — Justin L Zamory
(74) *Attorney, Agent, or Firm* — Hollingsworth Davis, LLC

(57) ABSTRACT

Described is a lock connection device for medical fluid lines comprising a first connector for coupling a first medical fluid line and a second connector for coupling a second medical fluid line, wherein both connectors are adapted for releasable attachment to each other. The device comprises a first closing member adapted to be releasably attached to the first connector so as to close it, and a second closing member adapted to be releasably attached to the second connector so as to close it. The first and second closing members are configured to attach to each other. If the first closing member is attached to the first connector and the second closing member is attached to the first closing member and the second connector, the first closing member can be detached from the first connector wherein the second closing member remains attached to the first closing member and the second connector.

16 Claims, 3 Drawing Sheets

(51) Int. Cl.
*A61M 39/18* (2006.01)
*A61M 39/20* (2006.01)

(58) Field of Classification Search
CPC ..... A61M 2039/1072; A61M 2205/128; A61L 2202/123; F16L 37/084
See application file for complete search history.

(56) References Cited

U.S. PATENT DOCUMENTS

| | | |
|---|---|---|
| 2004/0199143 A1 | 10/2004 | Lauer |
| 2005/0224372 A1* | 10/2005 | Sasso .................... A61J 1/2093 206/219 |
| 2009/0232586 A1 | 9/2009 | Diodati et al. |
| 2010/0030074 A1* | 2/2010 | Imai .................. A61M 5/31501 600/432 |
| 2011/0060293 A1* | 3/2011 | Guala .................... A61M 39/10 604/246 |
| 2012/0042971 A1 | 2/2012 | Py |

* cited by examiner

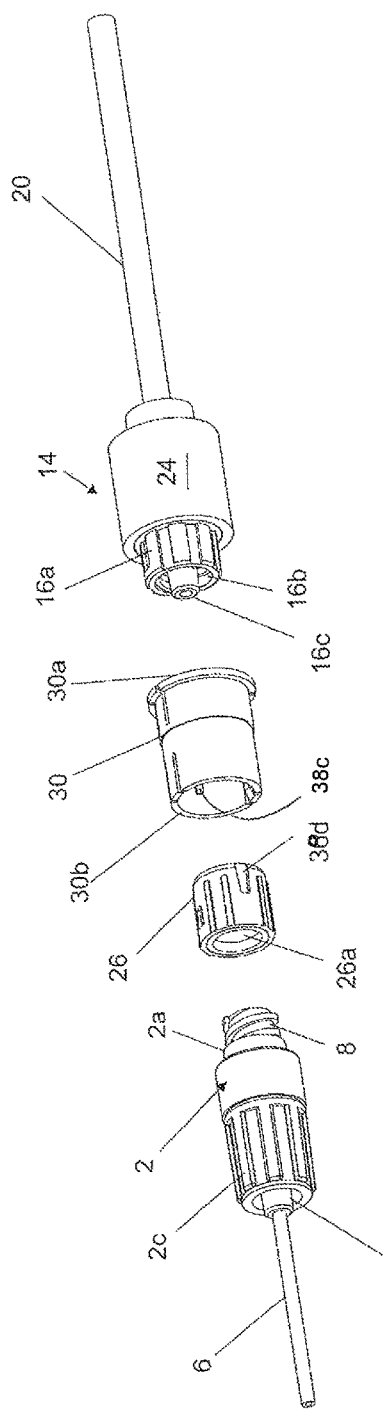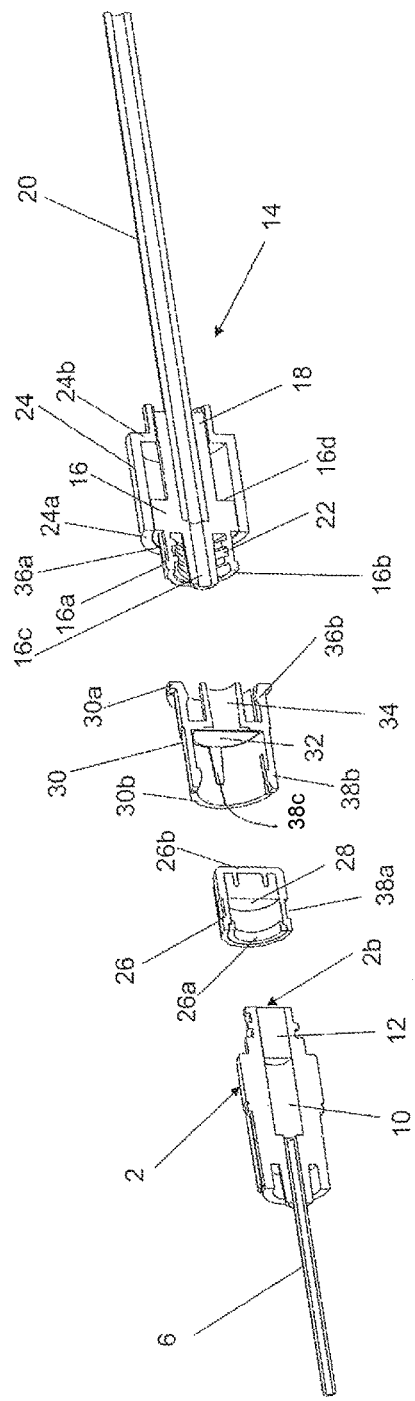

LOCK CONNECTION DEVICE FOR MEDICAL FLUID LINES

The present invention relates to a lock connection device for medical fluid lines.

In the prior art, pre-filled drug bags or pouches are connected to an infusion set so that they are required to be perforated by a spike or connected by a Luer connector in particular at their bottom. The infusion set is connected to a central venous catheter to be introduced into the patient's body. In particular for diseases wherein a central venous catheter is used, the risk of contamination is high so that extraordinary cleaning and preparation measures are required particularly at home to prevent contamination which otherwise would result in an undesired hospitalization of the patient. So, an infusion preparation out of the home or hospital is not possible or at least hard to carry out, although cases like hydration due to hot weather or extra muscular effort require such an infusion.

It is an object of the present invention to provide an improved construction of a lock connection device for medical fluid lines in order to prevent contamination during the connection procedure.

In order to achieve the aforementioned and further objects, according to the present invention, there is provided a lock connection device for medical fluid lines, comprising
- a first connector including a first coupling means for coupling a first medical fluid line, a first engaging portion having a first opening, and a passageway extending from the first coupling means to the first opening so as to provide a fluid communication between the first opening and the first medical fluid line when coupled to the first coupling means,
- a second connector including a second coupling means for coupling a second medical fluid line, a second engaging portion having a second opening and adapted to cooperate with the first engaging portion for a releasable attachment of the second connector to the first connector with the second opening communicating with the first opening, a second passageway extending from the second opening to the second coupling means so as to provide a fluid communication between the second opening and the second medical fluid line when coupled to the second coupling means, and first engaging means,
- a first closing member adapted to be releasably attached to the first connector so as to close the first opening, and
- a second closing member adapted to be releasably attached to the second connector so as to close the second opening and comprising second engaging means adapted to cooperate with the first engaging means for attaching the second closing member to the second connector,
- wherein the first closing member further comprises third engaging means,
- wherein the second closing member further comprises fourth engaging means adapted to cooperate with the third engaging means for attaching the second closing member to the first closing member, and
- wherein the first to fourth engaging means are adapted so that, in case the first closing member is attached to the first connector and the second closing member is attached to the first closing member and the second connector, the first closing member can be detached from the first connector wherein the second closing member remains attached to the first closing member and the second connector.

Preferred embodiments of the present invention are defined in the dependent claims.

The preparation process for a parenteral infusion in many countries require a strict cleaning protocol prescribing the provision of a separate portion of a room, wearing double gloves, a water basin, cleaning hands, inserting a sterilized spike into the tube of the bag and priming the tubing by gravity, then clamping it, releasing the cap from the central venous catheter and the infusion set, removing the first gloves, cleaning the central venous catheter Luer lock connector by means of alcohol and coupling the two Luer lock connectors of the infusion set and the catheter to each other. Contact of the sterile parts of both the infusion set and the catheter by the hands of the user or other items like a table is avoided.

Under the teaching of the present invention, a medication or drug bag or pouch can be used which is pre-filled either through a pharmaceutical procedure or at a compounder, wherein also provided is a complete disposable mechanism or a specific infusion part of the disposable portion of a pump, and a tubing extension set needed up to the catheter at the patient's body as well as a valve at the end of the pouch and an inlet to the infusion tube for preventing the drug to impregnate the tube or the infusion set. This valve preferably has three operational positions, i.e. one for sterilization and infusion, another one for pre-filling from a specific inlet, and a still further one for blocking the drug. Preferably, the disposable set at the end of the tubing comprises an anti-syphon valve Luer connector which additionally is to be provided with a protection cap including a hydrophobic membrane which is permeable for air but not for liquid so that preferably the filling or priming of the tube with drug will terminate automatically at the end of the tube due to increase of pressure in the tube when the drug comes in contact with the membrane. So, the present invention ensures an aseptic process when supplying the drug, without the need to connect a spike to the bag or pouch.

For the aseptic connection to an implanted catheter at the patient's body, the present invention suggests a special form for the aforementioned cap with the hydrophobic membrane so as to enable encapsulation of the corresponding cap of the catheter, to remove it by means of a movement which can be rotational, and to remove it with two caps attached to each other back-to-back. Preferably, the so-called "cap" includes a stick on the side with sterile material which can be e.g. gauze and which the user wets by cleaning material. So, the connector of the catheter swab port at the patient's body is cleaned. The cleaning material can be preloaded and sterilized wherein a protective removable packaging can be provided which is removed just before use.

The assembly of the two caps attached to each other and comprising the cleaning member is thrown away without gripping it by the user's hand(s) but due to an operation of release and discharge by pressing a push button or moving a finger of the same hand which holds the base of the Luer lock connector.

Thereafter, the aseptic coupling of the infusion set Luer connector to the catheter Luer connector takes place without having any hand touch any connector.

The infusion set can be disposable. Further, it can be wrapped onto the pouch, protected by air-permeable Tyvek-type paper which peels away in the same manner as from a gelatine packaging of a common medical disposable packaging. So, the packaging remains sterile after the pouch filling process, wherein preferably there are two packaging layers on the pouch so that the first external one is removed during the compounding and filling of the pouch and the second internal one is removed when the pouch is to be used.

The medicine pouch may have one or more chambers or compartments and may be of various materials such as PVC, polypropylene, EVA or polyolefin or multi-layer film with oxygen and/or moisture barriers like EVOH, silicon dioxide or other materials, so that the concentration of the drug does not change and have a long shelf life and, hence, a high drug stability. The pouch may have internal bumps or other anomalies like stripes crosswise or parallel so that the passage of liquids does not get blocked due to a vacuum which otherwise occurs in smooth plastic sheets, so that it can be used in various directions during portable use.

If the pouch has more than one chamber or compartment, it allows the user to join some of the chambers or compartments by simply pulling two sheets as known in the prior art (joined detachment) in a single solution (classical process in parenteral nutrition), while different embodiments, depending on the treatment, may not be joined but are infused with a sequence of one chamber after the other.

In parenteral nutrition, e.g. some extra medicines are needed before infusion of food, and at the end thereof an infusion of anticoagulants like heparin is required. If these extra medicines are injected with a syringe as it is common in the prior art, the probability of infection is increased. Therefore, an infusion in sequence is proposed, and the multilayer sheet of the pouch helps storing drugs for a long period. For an infusion in sequence, there is a need for some kind of an outlet barrier for the chambers or compartments which can be activated manually and/or automatically. The automatic activation could be done by valves with successive increased opening vacuum wherein the first valve at a vacuum free opens, followed by valves at successively larger vacuum increments of e.g. 0.1 bar, i.e. 2nd 0.1<3rd 0.2<4th 0.3 etc.

Alternatively, an infusion can also be carried out with a variation in hydrostatic pressure, whereupon the one with the highest pressure is done at first and the one with the lowest at last.

In another embodiment, the disposable item may include valves or fuses in the successive chambers or compartments which open by means of actuator pins in the pump and preferably comprise a shape-memory alloy which retracts due to electric current or heating.

Activation by hand is useful if the user wants to stop the basic therapeutic substance and to finish the cleaning, in particular by using e.g. a stopcock.

Preferably the pouch comprises an RFID/NFC tag or a two-dimensional barcode with information regarding the medicine, the dose and possibly the patient's data.

When using a pump, an infusion protocol may be automatically provided which facilitates the work of the nurse and avoids medical errors.

A portable application (mobile app) for mobile phones with built-in NFC will be able in the near future to read the protocol from the label of the medicine or from the pump and display it or change it if the user has the required authorization and passwords.

In the following, a preferred embodiment of the present invention will be described with reference to the accompanying drawings, wherein FIG. 1 shows an expanded view of a lock connection device according to a preferred embodiment of the present invention.

FIG. 2 includes a similar expanded view as FIG. 1 wherein the components of the device are shown in longitudinal section.

Figure 3:
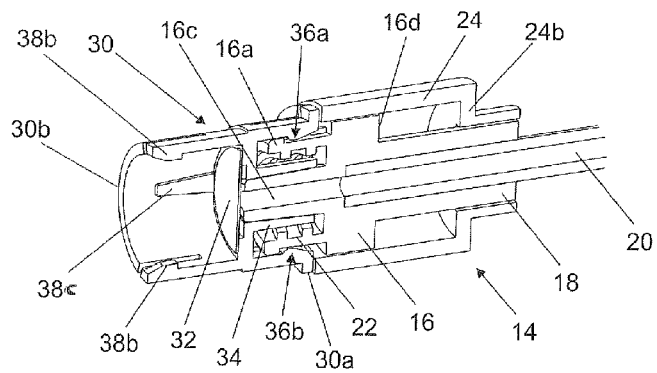
FIG. 3 shows an enlarged view of a male connector and a cap attached thereto in longitudinal section.
Figure 4:
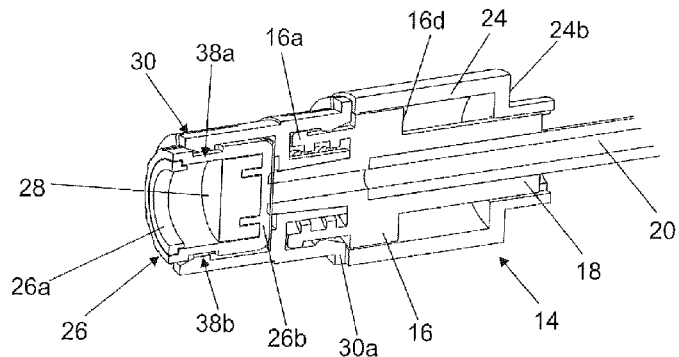
FIG. 4 shows an enlarged view of the male connector and two caps attached to each other and to the male connector in longitudinal section.

Firstly in particular with reference to FIGS. 1 to 4, all the components of the shown lock connection device according to a preferred embodiment of the present invention for medical fluid lines are described in detail.

The main components of the lock connection device are a female connector and a male connector which are adapted to be coupled to each other for providing a fluid connection between two medical fluid lines.

In the figures, reference numeral "2" generally indicates a female connector which comprises a first coupling means 4 for coupling a first medical fluid line 6 to the female connector 2. As further shown in the figures, the female connector 2 comprises an engaging portion 2a formed as a tubular protrusion which is arranged at the (according to the view of the figures right-hand) forward end of the female connector 2 opposite to the rear end including the first coupling means 4. The first engaging portion 2a is provided with an outer thread 8. Further, the first engaging portion 2a is open at its end face where an opening 2b is provided accordingly. Reference numeral "2c" indicates a (according to the view of the figures left-hand) back portion of the housing of the mail connector 2 where the first coupling means 4 is provided. As it becomes clear from FIG. 2, the female connector 2 further includes a tubular cavity 10 through which the first medical fluid line 6 communicates with the opening 2b. Within the cavity 10 of the female connector 2 arranged is a valve 12 whose function will be explained below in greater detail. Therefore, in the shown embodiment, the connector 2 may also be called a swabable connector which means that such kind of connector is able to block the fluid when not connected.

Figure 10:
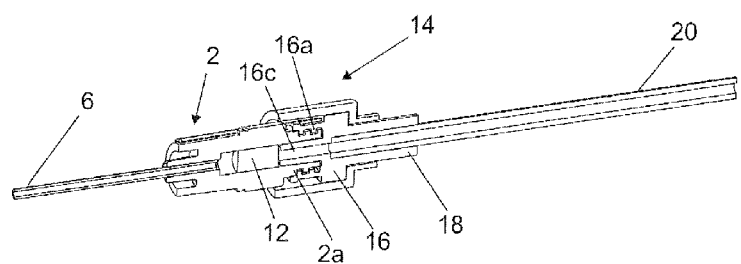
FIG. 10 shows the device in longitudinal section in a fifth and final operational mode wherein both the connectors are directly connected to each other.

As the further main component of the lock connection device, reference numeral "14" generally indicates a male lock connector having a body 16 which comprises at the (according to the view of the figures right-hand) rear end a second coupling means 18 for coupling a second medical fluid line 20. At its (according to the view of the figures left-hand) forward end the body 16 comprises an engaging portion 16a which is formed as a hollow tubular protrusion and open at its end face where an opening 16b is provided accordingly. As further shown in the figures, the engaging portion 16a of the male connector 14 is provided at its inner wall with an internal thread 22. The internal thread 22 of the male connector 14 matches with the outer thread 8 of the female connector 2 so that both the connectors 2 and 14 can be connected to each other by screwing accordingly, as shown in FIG. 10. However, it is understood that the coupling of the connectors 2, 14 can also be done without rotation but e.g. by snap-fit and spring action. As further shown in the figures, the body 16 of the male connector 14 comprises a small tube 16c which extends within the hollow engaging portion 16a to the opening 16b. The tube 16c, the coupling means 18 and the second medical fluid line 20 are arranged within the male connector 14 so that there is a fluid communication between the tube 16c and the second medical fluid line 20. Moreover, as shown in the figures, the male connector 14 comprises a slider 24 which is formed as a sleeve surrounding the body 16. The slider 24 is movable relative to the body 16 in longitudinal direction and, thus, in direction of the tube 16c.

Figure 5:
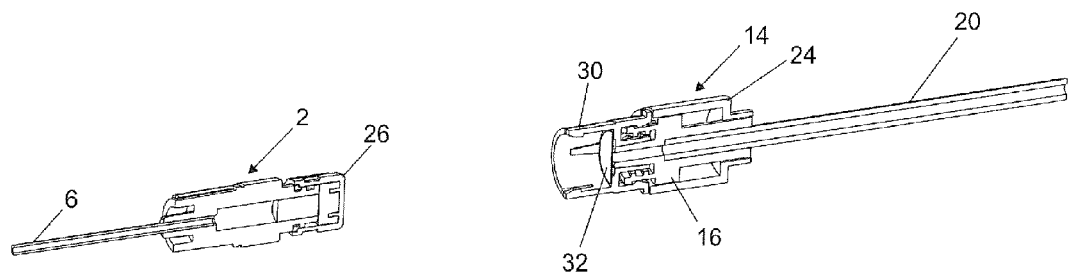
FIG. 5 shows the device in longitudinal section in a condition before starting the connection procedure wherein both the female connector and the male connector are separated from each other but each closed by a cap.

As particularly shown in the FIGS. 1 and 2, the lock connection device further comprises a first cap 26 having an open end 26a and a closed end 26b. The cap 26 is adapted to be attached onto the engaging portion 2a of the female connector 2 so that the engaging portion 2a of the female connector 2 extends into the cavity of the cap 26. This results in that the opening 2b of the engaging portion 2a of the female connector 2 is closed by the cap 26 as shown in FIG. 5. Furthermore, within the cavity of the cap 26 provided is compressible material 28 which is impregnated by a cleaning agent like alcohol; preferably a sponge can be used for this purpose. When attaching to the connector 2, the cap 26 locks to the engaging portion 2a so that the cleaning agent does not evaporate since the locking attachment is air-tight.

As further shown in the Figures, the lock connection device comprises a second cap 30 which is formed as a sleeve having a first open end 30a and a second open end 30b. In the shown example, the cavity of the second cap 30 is divided by a hydrophobic membrane 32 into a (according to the view of the figures right-hand) first portion communicating with the first open end 30a and a (according to the view of the figures left-hand) second portion communicating with the second open end 30b. As further shown in particular in FIG. 2, arranged within the cavity of the second cap 30 is a small tube 34 which is open at the first open end 30a and with its other end abuts the membrane 32 so that the tube 34 is closed by the membrane 32.

The second cap 30 is adapted to be attached to the engaging portion 16a of the male connector 14 wherein the second cap 30 with its first open end 30a is to be plugged onto the engaging portion 16a of the male connector 14, wherein at the same time the tube 16c is introduced into the tube 34 within the second cap 30. As a result, the opening 16b and the tube 16c of the male connector 14 is closed by the second cap 30, as shown in FIG. 5. For engagement with the second cap 30 in a water-tight manner, in the shown embodiment, the engaging portion 16a of the male connector 14 is provided at its outer side with a recess 36a with which retention lugs 36b are to be engaged, wherein the retention lugs 36b which are parts of the second cap 30 arranged at the first open end 30a and facing inwards as shown e.g. in FIG. 3 in greater detail.

Moreover, both the caps 26 and 30 are adapted to be attached to each other wherein the first cap 26 with its closed end 26b is to be plugged into the second open end 30b. The arrangement of both caps 26, 30 attached to each other is e.g. clearly shown in FIG. 9. For engagement with each other, in the shown embodiment, the first cap 26 is provided at its outer side with a recess 38a with which retention lugs 38b are to be engaged, wherein the retention lugs 38b are parts of the second cap 30, too, arranged at its second open end 30b and facing inwards as shown in particular in FIG. 4 in greater detail.

As in particular shown in the FIGS. 1 to 3, the second cap 30 is provided at its inner side with a longitudinal stem 38c or similar protrusion extending in longitudinal direction which is adapted to fit into and to be engaged with a longitudinal recess 38d which is provided at the outer side of the first cap 26 and also extends in longitudinal direction.

The recesses 36a, 38a and the associated retention lugs 36b, 38b may be preferably adapted so that a mutual longitudinal movement of the caps 26 and 30 and the connector 14 relative to each other is blocked, whereas the stem 38c and the recess 38d is adapted to block a rotational movement between both the caps 26 and 30.

In the following, the handling of the lock connection device whose structure has been described above for providing a medical fluid connection is now explained with reference to the FIGS. 5 to 10.

FIG. 5 shows the lock connection device in a condition before the start of the connection procedure, wherein the female and male connectors 2, 14 are still separated from each other with the female connector 2 being closed by the first cap 26 and the male connector 14 being closed by the second connector 30. In this condition, priming is carried out which is a procedure wherein the second medical fluid line 20 is filled with the drug. In order to avoid that air remains in the medical fluid line 20 and, hence, to avoid introduction of such air from the line 20 into a body during a later application, the membrane 32 takes care of that the air leaves the medical fluid line 20. Since the tube 16c and therefore the medical fluid line 20 is closed by the membrane 32, the leakage of the supplied medical fluid out of the medical fluid line 20 is prevented. However, since the membrane 32 is a hydrophobic membrane, air is allowed to pass through the membrane 32 and, hence, to leave the medical fluid line, whereas the medical fluid cannot pass through the hydrophobic membrane 32. When the medical fluid arrives at the hydrophobic membrane 32, the fluid pressure within the medical fluid line 20 will increase, and due to the increase of the fluid pressure a pump controller or a pump will give an alarm and/or the pump controller will stop the pump.

When handling the lock connection device it is important that the hands of a user do not touch the caps 26, 30 in order to avoid contamination which will otherwise be transferred into the medical fluid lines 6, 20 and, hence, into the medical fluid contained therein. Rather, it is important during the connecting procedure which will be described hereinafter, to remove the caps 26, 30 in an aseptical manner and to provide a direct coupling of both the female and male connectors 2, 14 in a sterile condition. So, it is necessary that during handling of the lock connection device and during the connecting procedure the user takes the one hand to only grip the back portion 2c of the female connector 2 and the other hand to only grip the slider 24 of the male connector 14.

Figure 6:
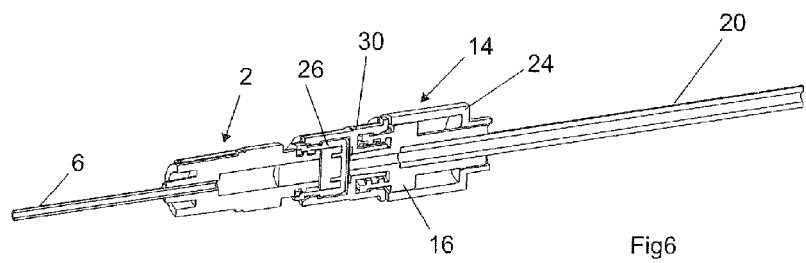
FIG. 6 shows the device in longitudinal section in a first operational mode of the connection procedure wherein the cap attached to the female connector is connected with the cap attached to the male connector.

When starting the connecting procedure, FIG. 6 shows a first operational mode of the device wherein the female and male connectors 2, 14 are coupled via the caps 26, 30. By doing so, the first cap 26 mounted to the female connector 2 is attached to the second cap 30 mounted to the male connector 14 in the manner as already described above.

Figure 7:
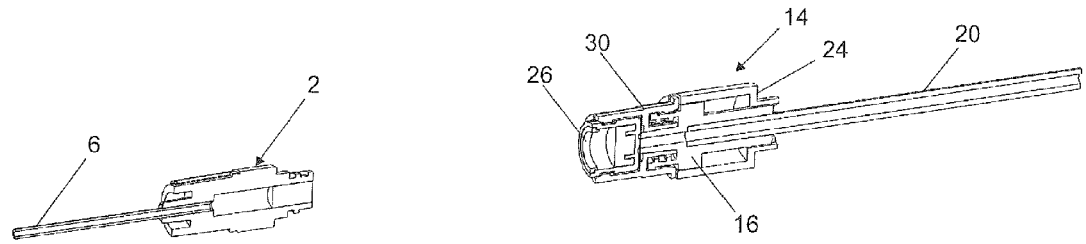
FIG. 7 shows the device in longitudinal section in a second operational mode during the connection procedure wherein the female connector is released from the arrangement of both the caps and the male connector attached to each other.

Thereafter, the female connector 2 is released from of the first cap 26 wherein the first cap 26 remains attached to the second cap 30 which again remains mounted to the male connector 14. In case the attachment of the first cap 26 at the engaging portion 2a of the female connector 2 is realized by screwing, preferably half-turn screwing, the release of the female connector 2 from the first cap 26, with the arrangement of the caps 26, 30 and the male connector 14 remaining attached to each other, is achieved by unscrewing the first cap 26 (to which the second cap 30 and the male connector 14 is attached) from the female connector 2. In an alternative embodiment, the release of the female connector 2 from the first cap 26 with the caps 26, 30 and the male connector 14 remaining attached to each other may be achieved by that the attachment of the first cap 26 to the female connector 2 is less tight than the attachment of the caps 26, 30 and the male connector 14 to each other. Namely, the engagement of the retention lugs 36b, 38b of the second cap in the recess 36a on the engaging portion 16a of the male connector 14 and the recess 38a of the first cap 26 and the engagement of the stem 38c in the recess 38d results in a relative tight attachment by effectively blocking any longitudinal and rotational movements. FIG. 7 shows the result of the above described step as a second operational mode wherein the female connector 2 is separated from the arrangement defined by both the caps 26 and 30 and the male connector 14 still attached to each other.

Figure 8:
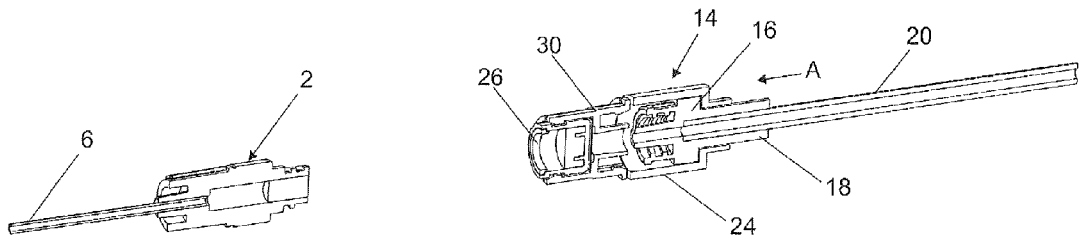
FIG. 8 shows the device in longitudinal section in a third operational mode during the connection procedure which differs from the second operational mode of FIG. 7 in that a slider of the male connector has been moved from a rearward position to a forward position and takes the arrangement of both the caps so that it is pushed away from the male connector.

Whereas the slider 24 has been in a rearward position so far as shown in the FIGS. 5 to 7 and also in the FIGS. 1 to 4, in a subsequent step the slider 24 is moved towards the second cap 30 to a forward position as shown in FIG. 8 in which the arrow "A" indicates the movement direction from their rearward position to the forward position. When the slider 24 is in its rearward position, its forward end 24a is already in contact with the first end 30a of the second cap 30 facing the male connector 14 as shown in the FIGS. 5 to 7 and also in the FIGS. 3 and 4. So, the movement of the slider 24 from its rearward position shown in the FIGS. 5 to 7 to its forward position shown in FIG. 8 results in that the second cap 30 is taken by the slider 24 and, hence, subject to the same movement in the direction A. Such a movement results in that the second cap 30 which is also attached to the first cap 26 is pulled off from the engaging portion 16a of the male connector 14 and, thus, released from the male connector 14. Of course, the force for moving the slider 24 against the second cap 30 must be such that the engagement of the retention lugs 36b with the recess 36a is overcome wherein the retention lugs 36b are arranged in a resilient manner and biased against their recess 36a. The movement of the slider 24 in the direction A is stopped when the rear end 24b of the slider 24 hits against a rear edge 16d of the body 16 of the male connector 14.

Alternatively, instead of the provision of a slider 24, the first end 30a of the second cap 30 can comprise a protrusion which may preferably have a cylindrical form corresponding to those of the slider and extends over the body 16 of the connector 14 so as to be pushed by a finger, in particular thumb, of the user for releasing the second cap 30 and, hence, the arrangement of the caps 26, 30 from the connector 14. In this alternative embodiment, preferably the protrusion is integral with the first end 30a of the second cap 30 so that there is only one part to manufacture and assemble.

Figure 9:
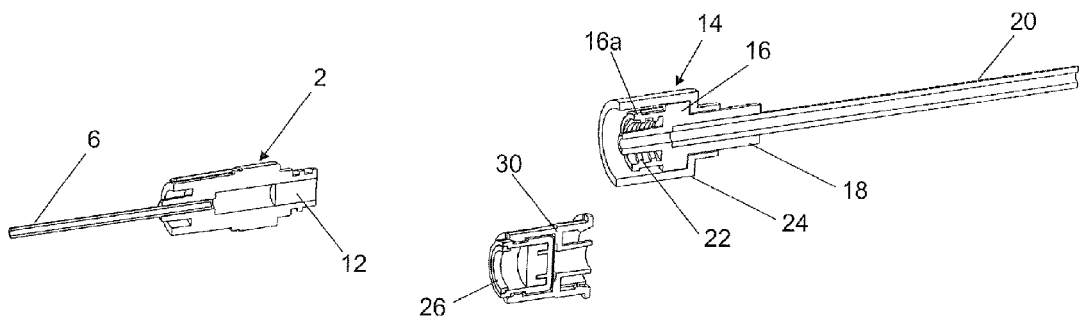
FIG. 9 shows the device in longitudinal section in a fourth operational mode during the connection procedure wherein the arrangement of both the caps attached to each other has been released from the male connector.

FIG. 9 shows the result of the aforementioned step wherein the arrangement of the caps 26, 30 still attached to each other are released and separated from the male connector 14 and, hence, from the remaining lock connection device.

Since now both the female and male connectors 2, 14 are 'freed' from the caps 26, 30 as shown in FIG. 9, both the female and male connectors 2, 14 are now ready to be directly coupled to each other. Since the coupling of both the connectors 2, 14 to each other is realized by screwing, preferably half-turn screwing, with the internal thread 22 of the male connector 14 being engaged with the outer thread 8 of the female connector 2, the male connector 14 is coupled to the female connector 2 by screwing accordingly. During the connecting procedure up to now as described above with reference to the FIGS. 5 to 9, the opening 2b of the female connector 2 has been closed by the swab valve 12. Now in the final step when the female connector 2 is directly coupled to the male connector 14, the tube 16c of the male connector 14 engages and actuates the valve 12, as schematically indicated in FIG. 10, so that the valve 12 opens with the result that a fluid communication between both the medical fluid lines 6, 20 via the cavity 10 of the female connector and the tube 16c of the male connector 14 is provided. FIG. 10 shows the female and male connectors 2, 14 in the 'directly coupled' final operational mode so that the medical fluid can now pass from the second medical fluid line 20 through the arrangement of the female and male connectors 2, 14 into the first medical fluid line 6.

As it becomes clear from the above, the second cap 30 according to the described preferred embodiment of the present invention is a special cap for two functions wherein the first function is to stop flow of medical fluid at the end of priming and the second function is to capture and remove the first cap 26 in an aseptical manner. Further, the special construction of the aforementioned device according to a preferred embodiment allows the arrangement of both the caps 26 and 30 to be rejected and released from the remaining device in an aseptical manner as well.

Since the above described embodiment of a lock connection device comprises as main components two connectors 2, 14 and two caps 26, 30, the device may also called an assembly.

Preferably, the above described embodiment of a lock connection device for medical fluid lines is provided as a Luer lock connection device wherein the female and male connectors 2, 14 are provided as Luer lock connectors and the threads 8 and 22 are so-called Luer lock threads so that both the connectors 2 and 14 can be connected to each other by screwing as standard Luer lock connectors usually achieving a half turn lock. So, preferably, the first cap 26 is of a standard half turn Luer lock connector type as well.

Preferably, the above described embodiment of the lock connection device for medical fluid lines can be part of an infusion set which is preferably permanently connected to a medication or drug bag to be pre-filled by a pharmaceutical company or compounder wherein any possibility of contamination from the upstream side is avoided. Furthermore, the bag can contain a pump mechanism, or the infusion set may contain a pumping segment for an infusion pump. Pre-filling of the bag can be done through a separate tubing at its bottom or via a three-way valve to be switched between a blocking position, an infusion and sterilization position and a filling position. Hence, a potentially infectious connection with a drug bag or pouch is avoided.

After all, to sum up, the connection with contamination prevention is performed by steps of a) mechanical priming of the set, b) sterile removal of both caps by capture of the one with the other and disposal of both caps by press rejection, and then c) coupling sterile connectors to each other.

In particular, the first medical fluid line 6 is connected to a central venous catheter extending into a patient's body and the second medical fluid line 20 is connected to a medication or drug bag or pouch without any hand of a user touching the front of any connector, but only their back or rear end so that an aseptic handling is ensured By using the above described embodiment of the lock connection device parenteral nutrition and other intravene infusions are allowed to be connected and carried out in non-aseptic locations like airports, stations, or at work. The medication or drug bag or pouch can be provided with a single compartment or with multiple compartments for not mixed drugs. Further provided is a pumping segment on the bag or pouch to be coupled through stop valves or clamps; alternatively, the pumping segment can be provided at the infusion set wherein a spike or Luer lock connector can be used for connection with the bag or pouch.

So, a complete solution is provided for intravenous infusion set connections with a central venous catheter long term protection by having an anti-contamination agent in a special cap, a pre-assembled bag and infusion set with upstream connection contamination being avoided, and automatic stop of purge of the infusion pump due to pressure increase, and leaving clean and non-contaminated connectors intact for a secure connection.

The invention claimed is:

1. A lock connection device for medical fluid lines, comprising:
    a first connector including a first coupling means for coupling a first medical fluid line, a first engaging portion having a first opening, and a passageway extending from the first coupling means to the first opening so as to provide a fluid communication between the first opening and the first medical fluid line when coupled to the first coupling means;
    a second connector including a second coupling means for coupling a second medical fluid line, a second engaging portion having a second opening and adapted to cooperate with the first engaging portion for a releasable attachment of the second connector to the first connector with the second opening communicating with the first opening, a second passageway extending from the second opening to the second coupling means so as to provide a fluid communication between the second opening and the second medical fluid line when coupled to the second coupling means, and first engaging means;
    a first closing member adapted to be releasably attached to the first connector so as to close the first opening; and
    a second closing member adapted to be releasably attached to the second connector so as to close the second opening and comprising second engaging means adapted to cooperate with the first engaging means for attaching the second closing member to the second connector,
    wherein the first closing member further comprises third engaging means,
    wherein the second closing member further comprises fourth engaging means adapted to cooperate with the third engaging means for attaching the second closing member to the first closing member, and
    wherein the first to fourth engaging means are adapted so that, in case the first closing member is attached to the first connector and the second closing member is attached to the first closing member and the second connector, the first closing member can be detached from the first connector wherein the second closing member remains attached to the first closing member and the second connector.

2. A lock connection device for medical fluid lines, comprising:
    a first connector including a first coupling means for coupling a first medical fluid line, a first engaging portion having a first opening, and a passageway extending from the first coupling means to the first opening so as to provide a fluid communication between the first opening and the first medical fluid line when coupled to the first coupling means;
    a second connector including a second coupling means for coupling a second medical fluid line, a second engaging portion having a second opening and adapted to cooperate with the first engaging portion for a releasable attachment of the second connector to the first connector with the second opening communicating with the first opening, a second passageway extending from the second opening to the second coupling means so as to provide a fluid communication between the second opening and the second medical fluid line when coupled to the second coupling means, and first engaging means and;
    a first closing member adapted to be releasably attached to the first connector so as to close the first opening; and
    a second closing member adapted to be releasably attached to the second connector so as to close the second opening and comprising second engaging means adapted to cooperate with the first engaging means for attaching the second closing member to the second connector, wherein the second connector further comprises releasing means adapted, in case the second closing member is attached to the second connector, to release the second closing member from the second connector,
    wherein the first closing member further comprises third engaging means,
    wherein the second closing member further comprises fourth engaging means adapted to cooperate with the third engaging means for attaching the second closing member to the first closing member, and
    wherein the first to fourth engaging means are adapted so that, in case the first closing member is attached to the first connector and the second closing member is attached to the first closing member and the second connector, the first closing member can be detached from the first connector wherein the second closing member remains attached to the first closing member and the second connector.

3. The device according to claim 2, wherein the second connector comprises a body including the second coupling means and the second engaging portion and further comprises as releasing means a sliding element which is movable relative to the body and adapted, in case the second closing member is attached to the second connector, to engage with the second closing member so as to push the second closing member away from the second connector and, hence, to release the second closing member from the second connector.

4. The device according to claim 3, wherein the sliding element is provided as a sleeve surrounding the body.

5. The device according to claim 2, wherein as releasing means a protrusion is provided at the second closing member which protrusion extends over or along the second connector when the second closing member is attached to the second connector.

6. The device according to claim 1, wherein one of the first and second closing members comprises a recess or cavity for accommodating at least a portion of the other of the first and second closing members.

7. The device according to claim 1, wherein the second closing member is provided as a sleeve which is closed by a hydrophobic membrane.

8. The device according to claim 1, wherein at least one of the first and second closing members is provided as a cap.

9. The device according to claim 1, wherein at least one of the first and second closing members includes a cleaning agent.

10. The device according to claim 9, wherein the first closing member includes compressible material, in particular a sponge, provided with the cleaning agent.

11. The device according to claim 1, wherein the one of the first and second engaging means of the second connector and the second closing member comprises a recess and the other of the third and fourth engaging means of the second closing member and the second connector comprises a retention lug adapted to releasably engage with said recess.

12. The device according to claim 1, wherein the one of the third and fourth engaging means of the first and second closing members comprises a recess and the other of the first and second engaging means of the first and second closing members comprises a retention lug adapted to releasably engage with said recess.

13. The device according to claim 1, wherein the one of the first and second engaging portions of the first and second connectors comprises an outer thread and the other of the first and second engaging portions of the first and second connectors comprises an internal thread.

14. The device according to claim 1, which is provided as a Luer lock connection device.

15. A disposable infusion set comprising a device according to claim 1 as well as a first medical fluid line coupled to the first connector, a second medical fluid line coupled to the second connector, and a medication or drug bag connected to at least one of the first and second medical fluid lines.

16. The disposable infusion set according to claim 15, wherein the medication or drug bag is a multi-compartment bag.

* * * * *